United States Patent [19]

Epstein et al.

[11] 4,193,933
[45] Mar. 18, 1980

[54] N-(2-FLUORO-1,1,2,2-TETRACHLOROE-THYLTHIO)-N-PHENYL METHANE SULFONAMIDES AND THEIR USE IN CONTROLLING PESTS

[75] Inventors: Peter F. Epstein, Overland Park, Kans.; Willis C. McGuire, Lafayette, Calif.

[73] Assignee: Stauffer Chemical Company, Westport, Conn.

[21] Appl. No.: 657,019

[22] Filed: Feb. 9, 1976

Related U.S. Application Data

[63] Continuation of Ser. No. 517,721, Oct. 24, 1974, abandoned, which is a continuation of Ser. No. 393,537, Aug. 31, 1973, abandoned, which is a continuation of Ser. No. 198,029, Nov. 9, 1971, abandoned, which is a continuation of Ser. No. 69,957, Sep. 4, 1970, abandoned, which is a continuation of Ser. No. 672,969, Oct. 5, 1967, abandoned, which is a continuation-in-part of Ser. No. 512,781, Dec. 9, 1965, abandoned.

[51] Int. Cl.² ............................................. C07C 119/00
[52] U.S. Cl. .............................. 260/453 RW; 424/298
[58] Field of Search ................... 260/453 RW; 71/98; 424/298

[56] References Cited

U.S. PATENT DOCUMENTS

| | | | |
|---|---|---|---|
| 2,779,788 | 1/1957 | Gysin et al. | 260/556 |
| 2,779,941 | 1/1957 | Gysin et al. | 260/556 |
| 3,178,447 | 4/1965 | Kohn | 260/309.5 |
| 3,344,153 | 9/1967 | Kühle et al. | 260/347.2 |

OTHER PUBLICATIONS

Kühle et al., "Fluorodichloromethylthio compounds etc.," (1964), Angew. Chem. 76, pp. 807–816 (Eng. Trans.) 1964.
Unterstenhoefer et al., "Acaricide compositions" (1964), CA61, pp. 13134–13135 (1964).

*Primary Examiner*—Glennon H. Hollrah
*Attorney, Agent, or Firm*—Edwin H. Baker

[57] ABSTRACT

Compounds of the formula

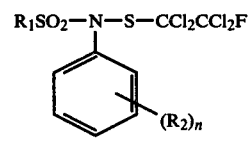

in which $R_1$ is a lower alkyl, lower haloalkyl or lower alkenyl group, $R_2$ is hydrogen, halogen, lower alkoxy, lower alkyl, cyano, or a nitro group, and n is an integer between 1 and 5, $R_2$ being the same or different when n is greater than 1; and their use in controlling pests, e.g. acarids, fungi, helminths and protozoa which cause coccidiosis.

1 Claim, No Drawings

N-(2-FLUORO-1,1,2,2-TETRACHLOROETHYLTHIO)-N-PHENYL METHANE SULFONAMIDES AND THEIR USE IN CONTROLLING PESTS

This is a continuation of application Ser. No. 517,721, filed Oct. 24, 1974, which is a continuation of application Ser. No. 393,537, filed Aug. 31, 1973, which is a continuation of application Ser. No. 198,029, filed Nov. 9, 1971, which is a continuation of application Ser. No. 69,957, filed Sept. 4, 1970, which is a continuation of application Ser. No. 672,969, filed Oct. 5, 1967, which is a continuation-in-part of application Ser. No. 512,781, filed Dec. 9, 1965, now abandoned.

This invention relates to certain new and novel (tetrachloro-fluoro-ethyl-thio)N-phenyl lower alkyl sulfonamides and their use in controlling pests. The compounds are particularly valuable for their pesticidal properties in controlling such pests as acarids, fungi, and especially helminths such as tapeworms and the like protozoa which cause coccidiosis.

More specifically, this invention relates to compounds of the formula

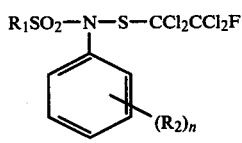

wherein $R_1$ is selected from the group consisting of lower alkyl, lower haloalkyl and lower alkenyl, and $R_2$ is selected from the group consisting of hydrogen, halogen, lower alkoxy, lower alkyl, cyano and nitro, and n is an integer between 1 and 5 preferably between 1 and 3, the $R_2$ groups being the same or different when n is between 2 and 5. By the terms lower alkyl, lower haloalkyl, lower alkoxy, we mean those members of said groups containing from 1 to 5 carbon atoms, inclusive. Similarly, by the term lower alkenyl we mean members of said group containing from 2 to 5 carbon atoms, inclusive.

A preferred compound of the compounds of the above formula is one in which $R_1$ is methyl, $R_2$ is hydrogen and n is 1.

The compounds herein contemplated can be prepared by several methods. One general method which can be applied in preparing the compounds is the condensation reaction between the appropriate substituted N-phenyl sulfonamide and 2-fluoro-1,1,2,2-tetrachloroethyl sulfenyl chloride. An acid acceptor, such as pyridine, triethylamine and the like, is used to facilitate the reaction. Any hydrogen chloride acceptor which preferably does not react with the reactants under the reaction conditions used can be employed. The reaction proceeds readily in the liquid phase. The employment of an inert organic solvent is also useful, facilitating processing as well as agitation of the reactants. Temperatures that permit operation in the liquid phase and which are between about 0° C. and reflux temperature of the solvent, if any is used, are employed. The reaction will proceed conveniently at low temperatures, usually about 10° C. or lower is used.

It has been found that the compounds of the present invention are effective as pesticidal agents. They are particularly effective in the control of acarids, fungi, protozoa which cause coccidiosis and especially helminth infections. Therefore the present invention contemplates the application of the compounds herein described in the control of pests.

The compounds of the present invention can be prepared in accordance with the following example.

EXAMPLE

Preparation of N-(2-fluoro-1,1,2,2-tetrachloroethylthio)-N-phenyl-methane sulfonamide To a mixture of N-phenyl methane sulfonamide (18.5 parts), triethylamine (10.1 parts) and chloroform (200 parts) was added with stirring below 10° C. 2-fluoro-1,1,2,2-tetrachloroethyl-1-sulfenyl chloride (23.5 parts) dissolved in chloroform (50 parts). After washing the resulting solution with three portions of water and removing the solvent, there was obtained as a product an initial 28.9 parts (76%) of a yellow solid. After recrystallization from ethanol or heptane there was obtained the title compound as a white solid, m.p. 98°–99.5° C. Analysis; percent calculated for $C_{10}H_{10}Cl_4FNO_2S_2$: C, 29.94; H, 2.51; Cl, 35.35; N, 3.49; S, 15.99. Found: C, 30.24; H, 2.73; Cl, 35.27; N, 3.35; S, 15.91.

The following is a table of the compounds prepared according to the aforedescribed procedures. Compound numbers have been assigned to each compound and are then used for identification throughout the balance of the application.

TABLE I

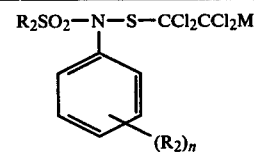

| Compound Number | $R_1$ | $R_2$ | n | m.p. °C. |
|---|---|---|---|---|
| 1* | $C_2H_5$ | H | 1 | 98–99.5 |
| 2 | $CH_3$ | 4-Cl | 1 | 92–93.5 |
| 3 | $CH_3$ | H | 1 | 65–67 |
| 4 | $ClCH_2$ | H | 1 | 66–68 |
| 5 | $n-C_3H_7$ | H | 1 | 84–84.5 |
| 6 | $ClCH_2$ | 2-$CH_3$ | 1 | 67–68.5 |
| 7 | $CH_2=CH$ | H | 1 | 79–80 |
| 8 | $C_2H_5$ | 4-CN | 1 | 81.5–82.5 |
| 9 | $ClCH_2$ | 4-Cl | 1 | 76–78 |
| 10 | $CH_3$ | 4-$CH_3$ | 1 | 71–73 |
| 11 | $ClCH_2$ | 4-$CH_3$ | 1 | ($n^{30}{}_D=1.5630$) |
| 12 | $C_2H_5$ | 4-Cl | 1 | 93.5–94.5 |
| 13 | $CH_3$ | 4-$NO_2$ | 1 | 107–108.5 |
| 14 | $CH_3$ | 2-Cl | 1 | 94.5–96.5 |
| 15 | $CH_3$ | 3-Cl | 1 | 79–80 |
| 16 | $CH_3$ | 4-$CH_3O$ | 1 | 105–106 |
| 17 | $CH_3$ | 2-$CH_3O$ | 1 | 124–124.5 |
| 18 | $CH_3$ | 4-F | 1 | 63–65 |
| 19 | $CH_3$ | 4-Br | 1 | 103–104 |
| 20 | 1-$C_3H_7$ | H | 1 | 72.5–73.5 |
| 21 | 1-$C_4H_9$ | 4-Cl | 1 | 63–64 |
| 22 | $CH_2=CH_2$ | 4-Cl | 1 | 72–76 |
| 23 | $CH_3$ | 2,4-$Cl_2$ | 2 | 66–70 |
| 24 | $n-C_4H_9$ | 2$CH_3$, 5-Cl | 2 | ($n^{30}{}_D=2.5535$) |
| 25 | $CH_2=CH_2$ | 2-$CH_3$, 5-Cl | 2 | 80.5–82 |
| 26 | $C_2H_5$ | 2-$CH_3$ 5-Cl | 2 | 79.81 |
| 27 | $C_2H_5$ | 2,4-$Cl_2$ | 2 | 77–78 |
| 28 | $CH_3$ | 2-$CH_3$, 5-Cl | 2 | 87–88 |
| 29 | $CH_3$ | 2-$CH_3$, 4-Cl | 2 | 88–90 |
| 30 | $CH_3$ | 2-$CH_3$, 3-Cl | 2 | 83.5–84 |
| 31 | $CH_3$ | 3-$CH_3$, 2-Cl | 2 | 73–74 |
| 32 | $CH_3$ | 3-$CH_3$ 4-Cl | 2 | 54–56 |
| 33 | $CH_3$ | 5-$CH_3$, 2-Cl | 2 | 86–87.5 |
| 34 | $CH_3$ | 2,3-$Cl_2$ | 2 | 97–98.5 |
| 35 | $CH_3$ | 2.5-$Cl_2$ | 2 | 116–117.5 |

TABLE I-continued

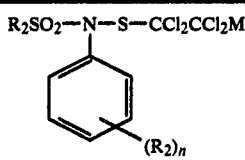

$R_2SO_2-N-S-CCl_2CCl_2M$ $(R_2)_n$

| Compound Number | $R_1$ | $R_2$ | n | m.p. °C. |
|---|---|---|---|---|
| 36 | $CH_3$ | 2,6-$Cl_2$ | 2 | 99.5–100.5 |
| 37 | $CH_3$ | 3,4-$Cl_2$ | 2 | 66.5–68 |
| 38 | $CH_3$ | 3,5-$Cl_2$ | 2 | 102.5–103.5 |
| 39 | $CH_3$ | 4,Cl, 2-$NO_2$ | 2 | 93.5–94.5 |
| 40 | $CH_3$ | 2-$CH_3$, 4-$NO_2$ | 2 | 80–83 |
| 41 | $CH_3$ | 2-$CH_3$, 5-$NO_2$ | 2 | 101–102.5 |
| 42 | $CH_3$ | 2-$OCH_3$, 4-$NO_2$ | 2 | 159–160 |
| 43 | $CH_3$ | 2-$OCH_3$, 5-$NO_2$ | 2 | 131.5–133 |
| 44 | $CH_3$ | 4$OCH_3$, 2-$NO_2$ | 2 | 98–99 |
| 45 | $CH_3$ | 2,5-$(CH_2)_2$ | 2 | 69–70.5 |
| 46 | $CH_3$ | 2,6-$(CH_3)_2$ | 2 | 77.5–79 |
| 47 | $CH_3$ | 2,4-$(OCH_3)_2$ | 2 | 108–109 |
| 48 | $CH_3$ | 2,5-$(OCH_3)_2$ | 2 | 99.5–100.5 |
| 49 | $CH_3$ | 3,5-$(OCH_3)_2$ | 2 | 116.5–117.5 |
| 50 | $CH_3$ | 2-$OCH_3$, 5Cl | 2 | 144–145 |
| 51 | $CH_3$ | 4$OCH_3$, 3Cl | 2 | 91–92 |
| 52 | $CH_3$ | 2$OCH_3$, 5-$CH_3$ | 2 | 137–138.5 |
| 53 | $CH_3$ | 2,5-$(OCH_3)_2$, 4Cl | 3 | 119–120 |
| 54 | $CH_3$ | 2,4-$(OCH_3)_2$, 5Cl | 3 | 128–129 |
| 55 | $CH_3$ | 2,4,6-$Cl_3$ | 3 | 123–124 |

*Compound Number 1 prepared in the Example.

As previously mentioned, the herein described novel compositions are useful and valuable in controlling various pests. The compounds of this invention were tested against various pests in the following manner.

Animal Systemic Control of *Hymenelopis nana*

The infection known as helminthiasis involves infestation of the animal body and particularly the gastrointestinal tract with various species of parasitic worms. It is a very widespread and serious disease and the methods available for its treatment and prevention are not always satisfactory. The present invention contemplates an improved chemotherapeutic method for combating helminthic infections.

Evaluation of oral efficacy and safety of continuously administered test compounds was conducted in mice employing *Hymenelopis nana* (*H. nana*, Hn) (dwarf tapeworm) as the helminth infection. Young Swiss Albino laboratory mice were used as the host. Prior to the test initiation the candidate compounds were accurately weighed to suitable amounts, premixed in magnacel or powdered feed by hand using a mortar and pestle. Before being added to previously weighed amounts of feed necessary to provide a desired feed concentration the compound premix was remixed in a small amount of feed. Each sample of feed and test compound were mixed for 15–20 minutes in a shell blender or other similar mixing equipment.

On the day of the test initiation the above-described mice were weighed individually and allotted to groups of two or more mice per group. Allotment was made by random selection of animals from each weight classification so that the total weight and weight variations were approximately equal for each group. The groups were housed in 4"×9" or larger hardware cloth cages. They received ad libitum feed and drinking water during the course of the 21–28 day evaluation period. All groups (medicated and unmedicated) received previously weighed amounts of feed on the first day of testing. Since the observation of helminth parasites in necropsied animals is facilitated by the absence of food from the small intestine, a 2–6 hour starvation period is imposed just prior to sacrifice of the survivors.

On the 2nd, or 3rd. day of medication the helminth infection was induced. *H. nana* eggs collected from fecal pellets of previously infected unmedicated host mice were used. Each test mouse to receive the infection was administered 0.1 to 0.5 ml. of a 0.05% carboxymethyl cellulose solution containing 100–300 eggs per mouse dose.

All mice found dead sufficiently intact during the test period were necropsied as soon as possible and the larvae or mature parasites counted. Between the 21st. and 28th. day all surviving mice were sacrificed and the contents of their intestines and ceca examined microscopically for parasites. The number of parasites found was recorded for comparison with the comparably exposed unmedicated groups for efficacy evaluation.

The following table presents a summary of the activity of the compounds of the instant invention against *H. nana* in mice. The values are given as percent control of the test helminth at dietary levels in parts per million (p.p.m.).

TABLE II

| Compound Number | Percent control of *H. nana* at dietary levels in ppm | | |
|---|---|---|---|
| | 2000 | 1000 | 500 |
| 1 | — | 100 | 100 |
| 2 | — | 100 | 70 |
| 3 | — | 82 | 100 |
| 4 | — | 99 | 70 |
| 5 | — | 100 | 100 |
| 6 | — | 100 | 75 |
| 7 | — | 100 | 98 |
| 8 | — | 100 | 100 |
| 9 | — | 96 | — |
| 10 | — | 82 | 55 |
| 12 | — | 100 | 61 |
| 13 | — | 100 | 69 |
| 14 | — | 100 | 98 |
| 15 | — | 100 | 100 |
| 16 | — | 100 | 100 |
| 17 | — | 100 | 100 |
| 18 | — | 100 | 32 |
| 19 | — | 100 | 25 |
| 21 | 80 | — | 75 |
| 22 | — | 86 | 75 |
| 23 | — | 93 | 90 |
| 24 | 99 | 85 | — |
| 26 | 90 | 99 | 95 |
| 27 | — | 75 | — |
| 28 | — | 99 | 99 |
| 29 | 99 | — | — |
| 30 | 95 | — | — |
| 31 | 99 | — | — |
| 32 | — | 99 | — |
| 33 | 99 | — | — |
| 34 | 99 | 70 | — |
| 35 | 99 | — | — |
| 36 | 99 | — | — |
| 37 | 99 | — | — |
| 39 | 99 | — | — |
| 41 | 99 | — | — |
| 42 | 99 | — | — |
| 43 | 99 | — | — |
| 44 | 99 | — | — |
| 46 | 99 | — | — |
| 47 | 99 | — | — |
| 48 | 99 | — | — |
| 49 | — | 75 | — |
| 50 | — | 40 | — |
| 51 | 99 | — | — |
| 53 | 99 | — | — |
| 54 | 95 | — | — |

— = Not tested at this level

Upon further evaluation it was found that compound number 18 was 90 percent effective in controlling *H. nana* at 200 ppm. Similarly compound number 4 presented 60 percent control, number 7, 50 percent control and number 3, 40 percent control of the test helminth at 200 ppm.

Acaricidal Evaluation Test

The two-spotted mite, *Tetranychus telanius* (Linn.), was employed in tests for miticides. Young pinto bean plants in the primary leaf stage were used as the host plants. The yound pinto bean plants were infested with several hundred mites. Dispersions of candidate materials were prepared by dissolving 0.1 gram in 10 ml. of a suitable solvent, usually acetone. Aliquots of the toxicant solutions were suspended in water containing 0.0175% v/v Sponto 221 ®, an emulsifying agent, the amount of water being sufficient to give concentrations of active ingredient ranging from 0.25% to 0.001%. The test suspensions were then sprayed on the infested pinto bean plants. After seven days, mortalities of post-embryonic and ovicidal forms were determined. The percentage of kill was determined by comparison with control plants which had not been sprayed with the candidate compounds. The LD-50 value was calculated using well-known procedures. These values are reported under the columns "PE" and "Eggs" in Table III.

In Vitro Vial Test

As previously mentioned, the herein described compositions are microbiologically active compounds which are useful and valuable in controlling various bacteria and fungi. The compounds were tested to determine the microbiostatic efficacy when in contact with growing fungi or bacteria in an artificial medium. Two 1-ounce vials were partially filled with malt broth. The compound to be tested was placed in the vials at any desired concentration (expressed in parts per million) and mixed with the broth. The vials were inoculated with water suspensions of spores of *Aspergillus niger* and *Penicillium* sp. The bottles were then sealed and held for one week, after which time the growth of the organisms was observed and noted. The test was repeated using lower concentrations of the compounds being tested to determine the lowest concentrations that can be used and still offer some control of the growth of the organism. Table III shows the results of the in Vitro tests.

TABLE III

| Compound Number | Acaricidal Activity (% Concentration) | | In Vitro Test (p.p.m.) | |
|---|---|---|---|---|
| | PE | Eggs | Asperigillus niger | Penicillum Sp. |
| 1 | .008 | .008 | 5* | 5* |
| 2 | .003 | .005 | 5* | 5* |
| 3 | .003 | .01 | 5* | 5* |
| 4 | .003 | .01 | 5* | 5* |
| 5 | .007 | | .5 | |
| 6 | .007 | .03 | .05 | .25 |
| 7 | .008 | | | |
| 8 | .03 | .05 | .5 | 1 |
| 9 | .01 | .05 | .5 | 5 |
| 10 | .01 | .03 | .5 | 1 |
| 11 | .008 | .03 | .25 | 1 |
| 12 | .008 | .05 | .5 | 1 |
| 13 | | | .25 | 5 |
| 14 | .01 | .03 | .5 | 1 |
| 15 | .03 | .03 | .25 | 5 |
| 18 | .005 | .03 | .25 | 1 |

TABLE III-continued

| Compound Number | Acaricidal Activity (% Concentration) | | In Vitro Test (p.p.m.) | |
|---|---|---|---|---|
| | PE | Eggs | Asperigillus niger | Penicillum Sp. |
| 19 | .001 | .03 | .25 | 1 |
| 20 | .003 | >.05 | 0.5 | 0.5 |
| 21 | .01 | .03 | 50 | 50 |
| 22 | .03 | .03 | 0.5 | 0.5 |
| 23 | .01 | .03 | 1.0 | 5 |
| 24 | .01 | .03 | 10 | 25 |
| 25 | .008 | >.05 | 1.0 | 5 |
| 26 | .005 | .03 | 1.0 | 1.0 |
| 27 | .03 | .03 | 0.5 | 0.25 |
| 28 | .005 | .03 | 0.5 | 0.25 |
| 29 | .005 | .03 | 0.5 | 0.25 |
| 30 | .005 | .03 | 0.5 | 0.25 |
| 31 | .005 | .03 | 50 | 50 |
| 32 | .005 | .03 | 0.25 | 0.25 |
| 33 | .005 | .03 | 0.5 | 0.25 |
| 34 | .001 | .03 | 0.25 | 0.25 |
| 35 | .005 | >.05 | 0.25 | 0.25 |
| 36 | .003 | .008 | 0.5 | 0.5 |
| 37 | .03 | .03 | 0.5 | 0.25 |
| 38 | .008 | .03 | 0.5 | 0.25 |
| 39 | .01 | >.05 | 1.0 | 0.5 |
| 40 | .03 | >.05 | 1.0 | 0.5 |
| 41 | >.05 | >.05 | 0.5 | 0.25 |
| 42 | >.05 | >.05 | 5 | 0.5 |
| 43 | >.05 | >.05 | .5 | 1.0 |
| 44 | .03 | >.05 | 1.0 | 0.25 |
| 45 | .005 | >.05 | 0.5 | 0.25 |
| 46 | .005 | >.05 | 1.0 | 0.25 |
| 47 | >.03 | >.05 | 5 | 5 |
| 48 | .01 | >.05 | 5 | 1.0 |
| 49 | >.05 | >.05 | 1.0 | 1.0 |
| 50 | .05 | >.05 | >50 | >50 |
| 51 | .03 | >.05 | 1.0 | 0.5 |
| 52 | .05 | >.05 | >50 | >50 |
| 53 | .05 | >.05 | 5 | 10 |
| 54 | >.05 | >.05 | 5 | 5 |
| 55 | .01 | .05 | 0.25 | 0.5 |

* = Lowest concentration tested

The compounds herein disclosed also displayed fungicidal activity against certain soilborne pathogenic fungi when tested in a soil fungicide incorporation test. Compound number 1 was found to give partial control as low as 10 p.p.m against *Rhizoctonia solani* and complete control at 10 p.p.m. of *Fusarium solani*. At 13 p.p.m. compound number 3 gave complete control of *Fusarium solani*.

Treatment and control of Coccidiosis

Coccidiosis is a common and widespread poultry disease caused by microorganisms, that is, several species of protozoan parasites of the genus Eimeria, such as *E. tenella, E. necatrix, E. acervulina, E. maxima, E. hagani,* and *E. brunetti. E. tenella* is the causative agent of a severe and often fatal infection of the caeca of chickens, which is manifested by severe and extensive hemorrhage, accumulation of blood in the caeca, passage of blood in the droppings. *E. necatrix* attacks the small intestine of the chick causing what is known as intestinal coccidiosis. Related species of the coccidia such as *E. meleagridis* and *E. adenoides* are causative organisms of coccidiosis in turkeys. When left untreated, the severe forms of coccidiosis lead to poor weight gain, reduced feed efficiency and high mortality in fowl. The elimination or control of this disease is, therefore, of paramount importance to the poultry raising industry. Coccidiosis also effects animals as well as poultry, for example, *E. zurnii, E. bovis* and *E. ellipsoidalis* are species of coccidia which have been described from cattle. There also appear to be at least seven valid species of coccidiosis in sheep and goats and at least six species of coccidiosis in swine. So it may be seen that there is also a need for effective coccidiostats in the animal raising industry.

Coccidiosis Test

SCW Leghorn chicks from a single age, breed and source are housed in isolated coccidia-free areas and fed ad libitum, a commercial 20 percent mash diet until they are from 10 to 21 days old. When these chicks reach the age of 10 to 21 days, age of maximum coccidiosis susceptibility, from 4 to 8 chicks are placed in heated hardware cloth cages. Selection of the chick is made at random from several weight classifications so that the total weight variations are approximately equal.

During the test interval of 10 to 14 days, certain groups of the chicks are fed medicated mash prepared by mixing a candidate compound into the mash at several concentrations such as 2000, 1000 or 500 p.p.m. Another group of chicks receive the same amount of mash unmedicated.

For initial evaluation against coccidia, on the second through the fifth day of the test interval, a single infection with 50,000 to 100,000 sporulated oocyster of *E. tenella* suspended in two ml. of water, is introduced directly into the chicks crops (both medicated and unmedicated groups) with a dosing syringe and blunt needle.

After 10 days, the chicks of the test are sacrificed. During the test, unmedicated, uninfected groups are maintained as controls.

The results obtained using certain of the compounds of this invention are reported in Table IV. Under the heading "No. Surv./No. Used", the values under "T" show the number of chicks (medicated and infected) that survived, out of the number used. The values under the heading "% Efficacy" were calculated by standard methods.

TABLE IV

| Compound Number | Dosage (ppm) | No. Surv./No. Used T | No. Surv./No. Used IC | Efficacy (%) Based on Mortality Et | Efficacy (%) Based on Lesion Score Et |
|---|---|---|---|---|---|
| 8 | 2000 | 5/5 | 8/10 | 100 | 75 |
| 10 | 1500 | 5/5 | 4/10 | 100 | 60 |
|  | 700 | 5/5 | 3/5 | 100 | 75 |
| 12 | 2000 | 10/10 | 16/20 | 100 | 90 |
|  | 500 | 20/20 | /25 | 100 | 60 |
| 13 | 2000 | 5/5 | 8/10 | 100 | 100 |
| 14 | 3000 | 5/5 | 9/10 | 100 | 80 |
| 18 | 2000 | 5/5 | 8/10 | 100 | 90 |
|  | 1000 | 20/20 | 22/30 | 100 | 15 |
| 20 | 2000 | 5/5 | 4/10 | 100 | 50 |
|  | 1000 | 5/5 | 4/10 | 100 | 50 |
| 21 | 2000 | 10/10 | 16/20 | 100 | 75 |
|  | 1000 | 5/5 | 8/10 | 100 | 30 |
| 22 | 1000 | 5/5 | 8/10 | 100 | 30 |
| 23 | 1000 | 9/10 | 14/20 | 20 | 70 |
| 24 | 2000 | 10/10 | 16/20 | 100 | 45 |
|  | 1000 | 5/5 | 8/10 | 100 | 45 |
| 25 | 1000 | 5/5 | 8/10 | 100 | 25 |
| 26 | 2000 | 5/5 | 8/10 | 100 | 75 |
|  | 1000 | 10/10 | 16/20 | 100 | 65 |
| 27 | 2000 | 5/5 | 5/10 | 100 | 35 |
| 28 | 2000 | 5/5 | 9/10 | 100 | 100 |
|  | 1000 | 15/15 | 17/25 | 100 | 70 |
| 29 | 2000 | 10/10 | 13/20 | 100 | 85 |
| 30 | 2000 | 10/10 | 14/20 | 100 | 60 |
|  | 1000 | 5/5 | 4/10 | 100 | 75 |
| 31 | 2000 | 5/5 | 8/10 | 100 | 80 |
| 32 | 2000 | 5/5 | 8/10 | 100 | 75 |
|  | 1000 | 5/5 | 4/10 | 100 | 60 |
| 33 | 2000 | 10/10 | 11/15 | 100 | 90 |
|  | 1000 | 10/10 | 15/20 | 100 | 55 |
| 34 | 1000 | 10/10 | 10/20 | 100 | 60 |
| 35 | 2000 | 10/10 | 13/20 | 100 | 65 |
|  | 1000 | 10/10 | 15/20 | 100 | 65 |
| 36 | 2000 | 5/5 | 5/10 | 100 | 40 |
| 37 | 1000 | 10/10 | 15/20 | 100 | 70 |
| 38 | 2000 | 5/5 | 5/10 | 100 | 60 |
|  | 1000 | 10/10 | 15/20 | 100 | 45 |
| 39 | 2000 | 5/5 | 4/10 | 100 | 85 |
| 40 | 2000 | 5/5 | 5/10 | 100 | 25 |
| 41 | 2000 | 10/10 | 13/20 | 100 | 95 |
|  | 1000 | 10/10 | 15/20 | 100 | 70 |
| 42 | 2000 | 5/5 | 8/10 | 100 | 20 |
|  | 1000 | 5/5 | 4/10 | 100 | 75 |
| 43 | 2000 | 5/5 | 8/10 | 100 | 65 |
|  | 1000 | 5/5 | 4/10 | 100 | 75 |
| 44 | 1000 | 5/5 | 4/10 | 100 | 40 |
| 45 | 2000 | 5/5 | 8/10 | 100 | 100 |
|  | 1000 | 5/5 | 4/10 | 100 | 50 |
| 46 | 2000 | 5/5 | 8/10 | 100 | 100 |
|  | 1000 | 5/5 | 4/10 | 100 | 60 |
| 47 | 2000 | 5/5 | 8/10 | 100 | 70 |
|  | 1000 | 5/5 | 4/10 | 100 | 40 |
| 48 | 1000 | 5/5 | 4/10 | 100 | 40 |
| 49 | 2000 | 5/5 | 8/10 | 100 | 35 |
|  | 1000 | 5/5 | 4/10 | 100 | 70 |
| 50 | 2000 | 5/5 | 5/10 | 100 | 40 |
| 51 | 2000 | 5/5 | 8/10 | 100 | 90 |
|  | 1000 | 5/5 | 4/10 | 100 | 85 |
| 52 | 2000 | 5/5 | 5/10 | 100 | 60 |
| 53 | 1000 | 5/5 | 4/10 | 100 | 15 |
| 54 | 2000 | 5/5 | 5/10 | 100 | 40 |
| 55 | 1000 | 5/5 | 4/10 | 100 | 20 |

The compounds of the present invention may be used as effective pesticidal agents and may be applied in a variety of ways at various concentrations. In practice the compounds are usually formulated with an inert pesticidal adjuvant utilizing methods well known to those skilled in the art. The amount applied will depend upon the nature of the particular utility desired. The rate of application may also vary with the microbilogical insecticidal or anthelmintic use intended. In treating domesticated animals the compounds may be mixed with a nontoxic edible carrier to form a feed supplement which is then incorporated in the animal feed in the desired concentration, or they may be adminstered in unit dosage form which may take the form of a capsule, bolus, tablet, a liquid drench or injection. Actually any of the methods now used or available for treating animals infected with or susceptible to parasitic infections are satisfactory. The unit dosage formulation may be prepared by distributing the desired amount of anthelmintic in a pharmaceutically acceptable vehicle. In treating insects, fungi or bacteria they may be used in the forms of emulsions, non-aqueous solutions, wettable powders, vapors, dusts and the like, as may be best fitted to the particular utility. Specific methods of application to a pest habitat are well known to those skilled in the art of pest control.

Various changes and modifications may be made without departing from the spirit and scope of the invention described herein as will be apparent to those skilled in the art to which it pertains. It is accordingly intended that the present invention shall only be limited by the scope of the appended claims.

We claim:
1. The compound having the formula

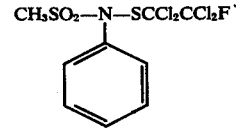

in which $R_1$ is methyl, $R_2$ is hydrogen and n is 1.

* * * * *

UNITED STATES PATENT AND TRADEMARK OFFICE
CERTIFICATE OF CORRECTION

PATENT NO. : 4,193,933

DATED : March 18, 1980

INVENTOR(S) : Peter F. Epstein et al.

It is certified that error appears in the above—identified patent and that said Letters Patent is hereby corrected as shown below:

Table I, the top line of the formula should read
---$R_1SO_2-N-S-CCl_2CCl_2F$---.

Table I, Compound 22, under the heading m.p. °C, please change "72-76" to read ---71-76---.

Table I, Compound 45, under the heading $R_2$, please change "2,5-$(CH_2)_2$" to read ---2,5-$(CH_3)_2$---.

UNITED STATES PATENT AND TRADEMARK OFFICE
CERTIFICATE OF CORRECTION

PATENT NO. : 4,193,933
DATED : March 18, 1980
INVENTOR(S) : Peter F. Epstein et al.

It is certified that error appears in the above—identified patent and that said Letters Patent is hereby corrected as shown below:

Table III, Compound 47, under the heading PE, please change " .03" to read --- .05---.

Column 8, Claim 1, the formula should be as follows:

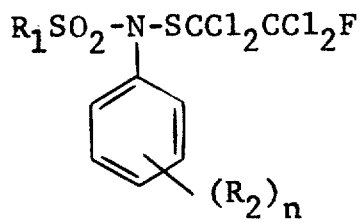

Signed and Sealed this

Ninth Day of February 1982

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : 4,193,933
DATED : March 18, 1980
INVENTOR(S) : Peter F. Epstein et al.

It is certified that error appears in the above—identified patent and that said Letters Patent is hereby corrected as shown below:

Table I, Compound 26, under the heading m.p. °C, please change "79.81" should read -- 79-81 --.

Signed and Sealed this

Eleventh Day of May 1982

[SEAL]

Attest:

GERALD J. MOSSINGHOFF

Attesting Officer   Commissioner of Patents and Trademarks